(12) United States Patent
Pawlak et al.

(10) Patent No.: US 8,193,254 B2
(45) Date of Patent: Jun. 5, 2012

(54) METHOD AND SYSTEM FOR METHANOL PRODUCTION

(75) Inventors: Nathan A. Pawlak, Marquette, MI (US); Walter Breidenstein, Boyne Falls, MI (US); Robert W. Carr, Bloomington, MN (US)

(73) Assignee: Gas Technologies LLC, Walloon Lake, MI (US)

( * ) Notice: Subject to any disclaimer, the term of this patent is extended or adjusted under 35 U.S.C. 154(b) by 0 days.

(21) Appl. No.: 12/959,902

(22) Filed: Dec. 3, 2010

(65) Prior Publication Data

US 2011/0127037 A1 Jun. 2, 2011

Related U.S. Application Data

(60) Division of application No. 11/526,824, filed on Sep. 25, 2006, now Pat. No. 7,910,787, which is a continuation-in-part of application No. 11/446,371, filed on Jun. 2, 2006, and a continuation-in-part of application No. 11/432,692, filed on May 11, 2006, and a continuation-in-part of application No. 11/351,532, filed on Feb. 10, 2006, now Pat. No. 7,642,293, said application No. 11/446,371 is a continuation-in-part of application No. 11/319,093, filed on Dec. 27, 2005, said application No. 11/432,692 is a continuation-in-part of application No. 11/319,093, said application No. 11/351,532 is a continuation-in-part of application No. 11/319,093.

(51) Int. Cl.
*C07C 27/00* (2006.01)

(52) U.S. Cl. ......... 518/700; 518/703; 518/705; 518/706

(58) Field of Classification Search .................. 518/700, 518/703, 705, 706
See application file for complete search history.

(56) References Cited

U.S. PATENT DOCUMENTS

| | | | |
|---|---|---|---|
| 1,038,547 A | 9/1912 | Fernekes |
| 1,500,080 A | 7/1924 | Kloppenburg |
| 1,776,771 A | 9/1930 | Boomer |
| 2,196,188 A | 4/1940 | Bone et al. |
| 2,384,028 A | 9/1945 | Hall |
| 2,467,993 A | 4/1949 | Rossman |
| 2,722,553 A | 11/1955 | Mullen, II et al. |
| 2,922,809 A | 1/1960 | Oberdorfer, Jr. |
| 3,027,411 A | 3/1962 | Murphy |
| 3,130,026 A | 4/1964 | Becker |
| 3,145,220 A | 8/1964 | Bartok |
| 3,232,991 A | 2/1966 | Magee |
| 3,483,229 A | 12/1969 | Bernard |
| 3,689,575 A | 9/1972 | Tarhan |
| 3,718,006 A | 2/1973 | Ranke et al. |
| 3,920,717 A | 11/1975 | Marion |
| 3,940,428 A | 2/1976 | Connell et al. |
| 3,975,172 A | 8/1976 | Ranke |
| 3,977,203 A | 8/1976 | Hinton et al. |
| 3,993,457 A | 11/1976 | Cahn et al. |
| 4,067,972 A | 1/1978 | Oswald et al. |
| 4,144,314 A | 3/1979 | Doerges et al. |
| 4,149,940 A | 4/1979 | Pinto |
| 4,152,407 A | 5/1979 | Fuchs |
| 4,203,915 A | 5/1980 | Supp et al. |
| 4,243,457 A | 1/1981 | Mayumi et al. |
| 4,243,613 A | 1/1981 | Brockhaus et al. |
| 4,252,548 A | 2/1981 | Markbreiter et al. |
| 4,271,086 A | 6/1981 | Supp et al. |
| 4,289,709 A | 9/1981 | Kaiser |
| 4,289,710 A | 9/1981 | Kaiser |
| 4,311,671 A | 1/1982 | Notman |
| 4,312,955 A | 1/1982 | Bartley |
| 4,324,567 A | 4/1982 | Ranke et al. |
| 4,346,179 A | 8/1982 | Sugier et al. |
| 4,353,712 A | 10/1982 | Marion et al. |
| 4,366,260 A | 12/1982 | Wainwright et al. |
| 4,374,288 A | 2/1983 | Scragg |
| 4,386,941 A | 6/1983 | Crouch et al. |
| 4,392,869 A | 7/1983 | Marion et al. |
| 4,394,137 A | 7/1983 | Marion et al. |
| 4,400,180 A | 8/1983 | Marion et al. |
| 4,430,316 A | 2/1984 | Ranke et al. |
| 4,443,560 A | 4/1984 | Le Blanc, Jr. et al. |
| 4,451,274 A | 5/1984 | O'Brien |
| 4,476,250 A | 10/1984 | Joyner et al. |
| 4,479,810 A | 10/1984 | Marion et al. |
| 4,490,156 A | 12/1984 | Marion et al. |
| 4,530,826 A | 7/1985 | Ohashi et al. |

(Continued)

FOREIGN PATENT DOCUMENTS

EP 0 790 226 A1 8/1997

(Continued)

OTHER PUBLICATIONS

"ASPECT Advanced Sustainable Processes by Engaging Catalytic Technologies—Call for Pre-proposals & Program Outline", Sep. 16, 2003, pp. 1-14.

Arutyunov, V., "Recent Results on Fast Flow Gas-Phase Partial Oxidation of Lower Alkanes", Journal of Natural Gas Chemistry 13 (2004), 13 pgs.

Bhatnagar, R. et al., "Methane Conversion in AC Electric Discharges at Ambient Conditions", Plenum Publishing, NY 1995, pp. 249-264.

Burch, et al., "Direct Conversion of Methane into Methanol", J. Chem. Soc., Faraday Trans. 1, 1989, 85(10), pp. 3561-3568.

Caldwell, T.A. et al., "Partial Oxidation of Methane to Form Synthesis Gas in a Tubular AC Plasma Reactor", Studies in Surface Science and Catalysis, vol. 36: Natural Gas Conversion VI, 2001, pp. 265-270.

(Continued)

*Primary Examiner* — Jafar Parsa

(74) *Attorney, Agent, or Firm* — Brooks Kushman P.C.

(57) ABSTRACT

An apparatus and method of producing methanol includes reacting a heated hydrocarbon-containing gas and an oxygen-containing gas in a reactor; to provide a product stream comprising methanol; and transferring heat from the product stream to the hydrocarbon-containing gas to heat the hydrocarbon containing gas. After removing methanol and $CO_2$ from the product stream, unprocessed hydrocarbons are mixed with the hydrocarbon containing gas for reprocessing through the reactor. Reactor byproducts are injected into the ground to increase the output of a hydrocarbon producing well.

29 Claims, 8 Drawing Sheets

U.S. PATENT DOCUMENTS

| | | | |
|---|---|---|---|
| 4,540,712 A | 9/1985 | Dombek |
| 4,564,643 A | 1/1986 | Shibata et al. |
| 4,575,387 A | 3/1986 | Larue et al. |
| 4,606,741 A | 8/1986 | Moreau et al. |
| 4,608,447 A | 8/1986 | Mazanec et al. |
| 4,609,388 A | 9/1986 | Adler et al. |
| 4,614,749 A | 9/1986 | Sapienza et al. |
| 4,618,732 A | 10/1986 | Gesser et al. |
| 4,619,946 A | 10/1986 | Sapienza et al. |
| 4,623,668 A | 11/1986 | Broecker et al. |
| 4,628,065 A | 12/1986 | Prouteau et al. |
| 4,628,066 A | 12/1986 | Bonnell et al. |
| 4,670,473 A | 6/1987 | Walker et al. |
| 4,721,458 A | 1/1988 | Conrad |
| 4,747,858 A | 5/1988 | Gottier |
| 4,760,210 A | 7/1988 | Sweeney |
| 4,782,096 A | 11/1988 | Banquy |
| 4,816,121 A | 3/1989 | Keefer |
| 4,822,393 A | 4/1989 | Markbreiter et al. |
| 4,861,360 A | 8/1989 | Apffel |
| 4,867,211 A | 9/1989 | Dodge et al. |
| 4,868,221 A | 9/1989 | Sie et al. |
| 4,873,267 A | 10/1989 | Sie et al. |
| 4,888,361 A | 12/1989 | Sie et al. |
| 4,982,023 A | 1/1991 | Han et al. |
| 5,012,029 A | 4/1991 | Han et al. |
| 5,015,798 A | 5/1991 | Han et al. |
| 5,063,250 A | 11/1991 | Murayama et al. |
| 5,067,972 A | 11/1991 | Hemmings et al. |
| 5,132,472 A | 7/1992 | Durante et al. |
| 5,177,279 A | 1/1993 | Harandi |
| 5,180,570 A | 1/1993 | Lee et al. |
| 5,220,080 A | 6/1993 | Lyons et al. |
| 5,384,335 A | 1/1995 | Tierney et al. |
| 5,496,859 A | 3/1996 | Fong et al. |
| 5,631,302 A | 5/1997 | Konig et al. |
| 5,735,936 A | 4/1998 | Minkkinen et al. |
| 5,770,630 A | 6/1998 | Kowal et al. |
| 5,861,441 A | 1/1999 | Waycuilis |
| 5,883,138 A | 3/1999 | Hershkowitz et al. |
| 5,886,056 A | 3/1999 | Hershkowitz et al. |
| 5,959,168 A | 9/1999 | van der Aalst et al. |
| 6,028,119 A | 2/2000 | Kokubu et al. |
| 6,102,987 A | 8/2000 | Gross et al. |
| 6,139,605 A | 10/2000 | Carnell et al. |
| 6,153,149 A | 11/2000 | Rabitz et al. |
| 6,159,432 A | 12/2000 | Mallinson et al. |
| 6,300,380 B1 | 10/2001 | Kobayashi et al. |
| 6,328,854 B1 | 12/2001 | Sherman et al. |
| 6,342,091 B1 | 1/2002 | Menzel et al. |
| 6,447,745 B1 | 9/2002 | Feeley et al. |
| 6,595,291 B1 | 7/2003 | Lia et al. |
| 6,625,988 B2 | 9/2003 | Weisenstein et al. |
| 6,632,971 B2 | 10/2003 | Brown et al. |
| 6,645,272 B2 | 11/2003 | Lemaire et al. |
| 6,667,347 B2 | 12/2003 | O'Rear et al. |
| 6,720,359 B2 | 4/2004 | O'Rear et al. |
| 6,726,850 B1 | 4/2004 | Reyes et al. |
| 6,736,955 B2 | 5/2004 | Shaw |
| 6,881,389 B2 | 4/2005 | Paulsen et al. |
| 6,881,758 B2 | 4/2005 | Guillard et al. |
| 6,942,719 B2 | 9/2005 | Stewart |
| 7,028,478 B2 | 4/2006 | Prentice, III |
| 7,067,558 B2 | 6/2006 | Grobys et al. |
| 7,071,238 B2 | 7/2006 | Gamlin et al. |
| 7,083,662 B2 | 8/2006 | Xu et al. |
| 7,108,838 B2 | 9/2006 | McGee |
| 2001/0006615 A1 | 7/2001 | Badano |
| 2002/0177741 A1 | 11/2002 | Allison et al. |
| 2003/0032844 A1 | 2/2003 | Seiki et al. |
| 2003/0065042 A1 | 4/2003 | Shaw |
| 2004/0065199 A1 | 4/2004 | Rojey et al. |
| 2004/0123523 A1 | 7/2004 | Rong et al. |
| 2004/0171701 A1 | 9/2004 | Shaw |
| 2006/0035986 A1 | 2/2006 | Bichkov et al. |
| 2006/0235088 A1 | 10/2006 | Olah et al. |
| 2006/0264683 A1 | 11/2006 | Knox et al. |

FOREIGN PATENT DOCUMENTS

| | | |
|---|---|---|
| GB | 2 159 153 A | 11/1985 |
| GB | 2 196 335 A | 4/1988 |
| JP | 63001438 A | 1/1988 |
| JP | 2004 315413 A | 11/2004 |
| RU | 2 162 460 C1 | 1/2001 |
| RU | 2 200 731 C1 | 3/2003 |
| RU | 2 203 261 C1 | 4/2003 |
| SU | 1 336 471 A1 | 9/1996 |
| SU | 1 469 788 A1 | 11/1996 |
| WO | 96/06901 A1 | 3/1996 |
| WO | 03/031380 A1 | 4/2003 |

OTHER PUBLICATIONS

Foulds, G. et al., "Kinetics, Catalysis, and Reaction Engineering—Homogeneous Gas-Phase Oxidation of Methane Using Oxygen as Oxidant in an Annular Reactor", Ind. Eng. Chem. Res. 1993, 32, pp. 780-787.

Gordon, C.L. et al., "Selective Hydrogenation of Acetylene to Ethylene During the Conversion of Methane in a Catalytic DC Plasma Reactor", Studies in Surface Science and Catalysis, vol. 36: Natural Gas Conversion VI, 2001, pp. 271-276.

Gordon, C.L. et al., "The Production of Hydrogen From Methane Using Tubular Plasma Reactors", Advances in Hydrogen Energy, 2000, pp. 57-67.

Henni, et al., "Solubility of Carbon Dioxide in Methyldiethanolamine + Methanol + Water", Journal of Chemical Engineering Data, 1995, 40, pp. 493-495.

Kanniche, M. et al., "Technico-Economical Feasibility Study of CO2 Capture, Transportation and Geo-Sequestration: A Case Study for France, Part 1: Comparison of the CO2 Capture Options in IGCC System", 2004, 5 pages.

Karavaev, M. M. et al., "Technology of Synthetic Methanol", Moscow, Chemistry, 1984 pp. 72-125.

Koert, D.N. et al., A flow reactor for the study of homogeneous gas-phase oxidation of hydrocarbons at pressure up to 20 atm (2MPa), Mar. 1992, 7 pgs.

Larkin, D.W. et al., "Production of Organic Oxygenates in the Partial Oxidation of Methane in a Silent Electric Discharge Reactor", Ind. Eng. Chem. Res. 2001, 40, pp. 1594-1601.

Larkin, D.W. et al., "Product Selectivity Control and Organic Oxygenate Pathways From Partial Oxidation of Methane in a Silent Electric Discharge Reactor", Ind. Eng. Chem. Res. 2001, 40, pp. 5496-5506.

Larkin, D.W. et al., "Carbon Pathways, Co2 Utilization, and In Situ Product Removal in Low Temperature Plasma Methane Conversion to Methanol", Greenhouse Gas Control Technologies, 1999, pp. 397-402.

Larkin, D.W. et al., "Oxygen Pathways and Carbon Dioxide Utilization in Methane Partial Oxidation in Ambient Temperature Electric Discharges", Energy & Fuels 1998, 12, pp. 740-744.

Liu, C. et al., "Experimental Investigations on the Interaction Between Plasmas and Catalyst for Plasma Catalytic Methane Conversion (PCMC) over Zeolites", Natural Gas Conversion V, Studies in Surface Science and Catalysis, Col. 119, 1998, pp. 361-366.

Liu, C. et al., "Oxidative Coupling of Methane with AC and DC Corona Discharges", Industrial & Engineering Chemistry Research, vol. 35, No. 10, 1996, pp. 3295-3301.

Liu, C. et al., "Nonoxidative Methane Conversion to Acetylene over Zeolite in a Low Temperature Plasma", Journal of Catalysis 179, 1998, pp. 326-334.

Liu, C. et al., "Modification of NaY Zeolite in a Corona Discharge and its Application for the Reduction of Carbon Dioxide", Greenhouse Gas Control Technologies, 1999, pp. 1103-1105.

Liu, C. et al., "Methane Conversion to Higher Hydrocarbons in a Corona Discharge Over Metal Oxide Catalysts with OH Groups", 1997, Applied Catalysis A: General 164, pp. 21-33.

Liu, C. et al., "Comparative Investigations on Plasma Catalytic Methane Conversion to Higher Hydrocarbons over Zeolites", Applied Catalysis A: General 178, 1999, pp. 17-27.

Lodeng, et al., "Experimental and Modeling Study of the Selective Homogeneous Gas Phase Oxidation of Methane to Methanol", Industrial Engineering Chemical Res., 1995, pp. 1044-1059.

Marafee, A. et al., "An Experimental Study on the Oxidative Coupling of Methane in a Direct Current Corona Discharge Reactor over Sr/La2O3 Catalyst", Industrial & Engineering Chemistry Research, vol. 36, No. 3, 1997, pp. 632-637.

Ranzi, E. et al., "A New Comprehensive Reaction Mechanism for Combustion of Hydrocarbon Fuels", Prepared for the Twenty-Fifth International Symposium on Combustion Jul. 31-Aug. 5, 1994, Dec. 3, 1993, 23 pgs.

Sheverdenkin, E.V. et al., "Kinetics of Partial Oxidation of Alkanes at High Pressures; Oxidation of Ethane and Methane-Ethane Mixtures", Theoretical Foundations of Chemical Engineering, vol. 38, No. 3, 2004, pp. 311-315.

Supat, K. et al., "Synthesis Gas Production From Partial Oxidation of Methane with Air in AC Electric Gas Discharge", Energy & Fuels, 2003, 17, pp. 474-481.

Supat, K. et al., "Combined Steam Reforming and Partial Oxidation of Methane to Synthesis Gas Under Electrical Discharge", Ind. Engr. Chem. Res., 2003, 42, Page Est: 7.2 (A-H).

Thanyachotpaiboon, K. et al., "Conversion of Methane to Higher Hydrocarbons in AC Nonequilibrium Plasmas", AIChE Journal, Oct. 1998, vol. 4, No. 10, pp. 2252-2257.

Zang, et al., "Recent Progress in Direct Partial Oxidation of Methane to Methanol", Journal of Natural Gas Chemistry, Vol. 12, No. 2, 2003, pp. 81-89.

METHOD AND SYSTEM FOR METHANOL PRODUCTION

CROSS-REFERENCE TO RELATED APPLICATIONS

This application is a divisional of U.S. patent application No. 11/526,824; filed on Sep. 25, 2006, now U.S. Pat. No. 7,910,787, issued Mar. 22, 2011, which is a continuation-in-part application of U.S. patent application No. 11/446,371, filed on Jun. 2, 2006, U.S. patent application No. 11/432,692, filed on May 11, 2006, and U.S. patent application No. 11/351,532, filed on Feb. 10, 2006, now U.S. Pat. No. 7,642,293 B2, issued Jan. 5, 2010. U.S. patent application Nos. 11/446,371 and 11/432,692 and 11/351,532 are continuation-in-part applications of U.S. patent application No. 11/319,093, filed on Dec. 27, 2005, Publication No. 2006/0122283 A1, published Jun. 8, 2006. The disclosures of the above applications are incorporated by reference.

BACKGROUND OF THE INVENTION

The present invention relates to a method of and an apparatus for producing methanol.

Methods and apparatuses for the conversion of methane into methanol are known. It is known to carry out a vapor-phase conversion of methane into a synthesis gas (mixture of CO and $H_2$) with its subsequent catalytic conversion into methanol as disclosed, for example, in Karavaev M. M., Leonov B. E., et al "Technology of Synthetic Methanol", Moscow, "Chemistry" 1984, pages 72-125. However, in order to realize this process it is necessary to provide complicated equipment, to satisfy high requirements for the purity of the gas, to spend high quantities of energy for obtaining the synthesis gas and for its purification, and to have a significant number of intermittent stages from the process. Also, for medium and small enterprises with the capacity of less than 2,000 tons/day it is not economically feasible.

Russian Patent No. 2,162,460 includes a source of hydrocarbon-containing gas, a compressor and a heater for compression and heating of the gas, and a source of oxygen-containing gas with a compressor. It further includes successively arranged reactors with alternating mixing and reaction zones and a means to supply the hydrocarbon-containing gas into a first mixing zone of the reactor and the oxygen-containing gas into each mixing zone, a recuperative heat exchanger for cooling of the reaction mixture through a wall by a stream of cold hydrocarbon-containing gas of the heated hydrocarbon-containing gas into a heater, a cooler-condenser, a partial condenser for separation of waste gasses and liquid products with a subsequent separation of methanol, a pipeline for supply of the waste gas into the initial hydrocarbon-containing gas, and a pipeline for supply of waste oxygen-containing products into the first mixing zone of the reactor.

In this apparatus, however, it is not possible to provide a fast withdrawal of heat of the highly exothermic oxidation reaction of the hydrocarbon-containing gas because of the inherent limitations of the heat exchanger. This leads to the necessity to reduce the quantity of supplied hydrocarbon-containing gas and, further, it reduces the degree of conversion of the hydrocarbon-containing gas. Moreover, even with the use of oxygen as an oxidizer, it is not possible to provide an efficient recirculation of the hydrocarbon-containing gas due to the rapid increase of the concentration of carbon oxides. A significant part of the supplied oxygen is wasted for oxidation of CO into $CO_2$, which additionally reduces the degree of conversion of the initial hydrocarbon-containing gas to useful products and provides a further overheating of the reaction mixture. The apparatus also requires burning an additional quantity of the initial hydrocarbon-containing gas in order to provide the utility needs of a rectification of liquid products. Since it is necessary to cool the gas-liquid mixture after each reactor for separation of liquid products and subsequent heating before a next reactor, the apparatus is substantially complicated and the number of units is increased.

A further method and apparatus for producing methanol is disclosed in the patent document RU 2,200,731, in which compressed heated hydrocarbon-containing gas and compressed oxygen-containing gas are introduced into mixing zones of successively arranged reactors, and the reaction is performed with a controlled heat pick-up by cooling of the reaction mixture with water condensate so that steam is obtained, and a degree of cooling of the reaction mixture is regulated by parameters of escaping steam, which is used in liquid product rectification stage.

Other patent documents such as U.S. Pat. Nos. 2,196,188; 2,722,553; 4,152,407; 4,243,613; 4,530,826; 5,177,279; 5.959,168 and International Publication WO 96/06901 disclose further solutions for transformation of hydrocarbons. It is believed that the existing methods and apparatus for producing methanol can be further improved.

SUMMARY

It is accordingly an object of the present invention to provide a method of and an apparatus for producing methanol, which is a further improvement of the existing methods and apparatuses.

It is another feature of the present teachings to provide a method of and an apparatus for producing methanol which can be used with minimal processing of gas and gas-condensate deposits, and also at any gas consumer, such as power plants, gas distributing and gas reducing stations, chemical production facilities, etc., or small methane producers, (i.e., coal mines, oil production (flares), landfills, farms.)

In keeping with these objects and with others which will become apparent hereinafter, one feature of the present invention resides, briefly stated, in a method of producing methanol, which includes the steps of supplying into a reactor a hydrocarbon-containing gas stream, supplying into the reactor an oxygen containing gas; carrying out in the reactor an oxidation of the hydrocarbon-containing gas by oxygen of said oxygen-containing gas; and, after removing impurities and products of the reaction, recycling un-reacted hydrocarbon gas into the hydrocarbon-containing gas stream for further reaction.

Another feature of the present teachings is an apparatus for producing methanol, which has a reactor for receiving and reacting a hydrocarbon-containing gas stream from a well or other source with an oxygen-containing gas, to carry out in the reactor oxidation of the heated hydrocarbon-containing gas by oxygen of said oxygen-containing gas. The apparatus also has a mechanism for supplying into the reactor a non-oxidizing coolant to be directly mixed with a mixture of said heated hydrocarbon containing gas and said oxygen containing gas at a later stage of the reaction to inhibit the further oxidation and decomposition of formaldehyde. Un-reacted hydrocarbon-containing gas is then processed to remove products and contaminants before being recycled back into the hydrocarbon-containing gas stream. Reaction byproducts, such as $CO_2$, can be injected into the ground at a predetermined distance from a well to increase the output of the well.

As can be seen, in accordance with the present teachings, a heated hydrocarbon-containing gas stream and oxygen-containing gas are supplied into a reaction zone or into a reactor, where a gas phase oxidation of the hydrocarbon-containing gas is performed at elevated temperature and pressure in the reaction zone. The reaction mixture is cooled and then is separated into waste gas and liquid product. The waste gas is scrubbed to remove $CO_2$ and formaldehyde and returned to the heated hydrocarbon-containing gas stream. Cold hydrocarbon-containing gas is supplied into a regulation zone of the reactor to reduce the temperature of the hydrocarbon-containing gas thereby to provide a redistribution of the ratio of products to produce corresponding quantities of methanol and formaldehyde. Methanol produced can then be injected into a natural gas stream to reduce the formation of hydrates within the pipeline.

In accordance with the present teachings, during cooling of the reaction mixture in the partial condenser, heat is transmitted to an input stream supplied into a formaldehyde rectification column for performing rectification of formaldehyde and simultaneous regeneration of the primary scrubber solvent, methanol. Within the partial condenser, dry gas is separated from raw liquids, including methanol, ethanol, and water. The raw liquids, through the flash drum, are supplied into a rectification column. The temperature of the top of the column is, between about 70 and about 75° C., the pressure in the column is, for example, up to 0.2 MPa. The final product is supplied to storage or further processing. The dry gas is scrubbed to remove $CO_2$ and formaldehyde and is then returned to the reactor in the hydrocarbon input stream. $CO_2$ can then be injected into the ground at a predetermined distance from a well to increase the output of the well.

The novel features which are considered as characteristic for the present invention are set forth in particular in the appended claims. The invention itself, both as to its construction and its method of operation together with additional objects and advantages thereof, will be best understood from the following description of specific embodiments when read in connection with the accompanying drawings.

DESCRIPTION OF THE PREFERRED EMBODIMENTS

Figure 1A:
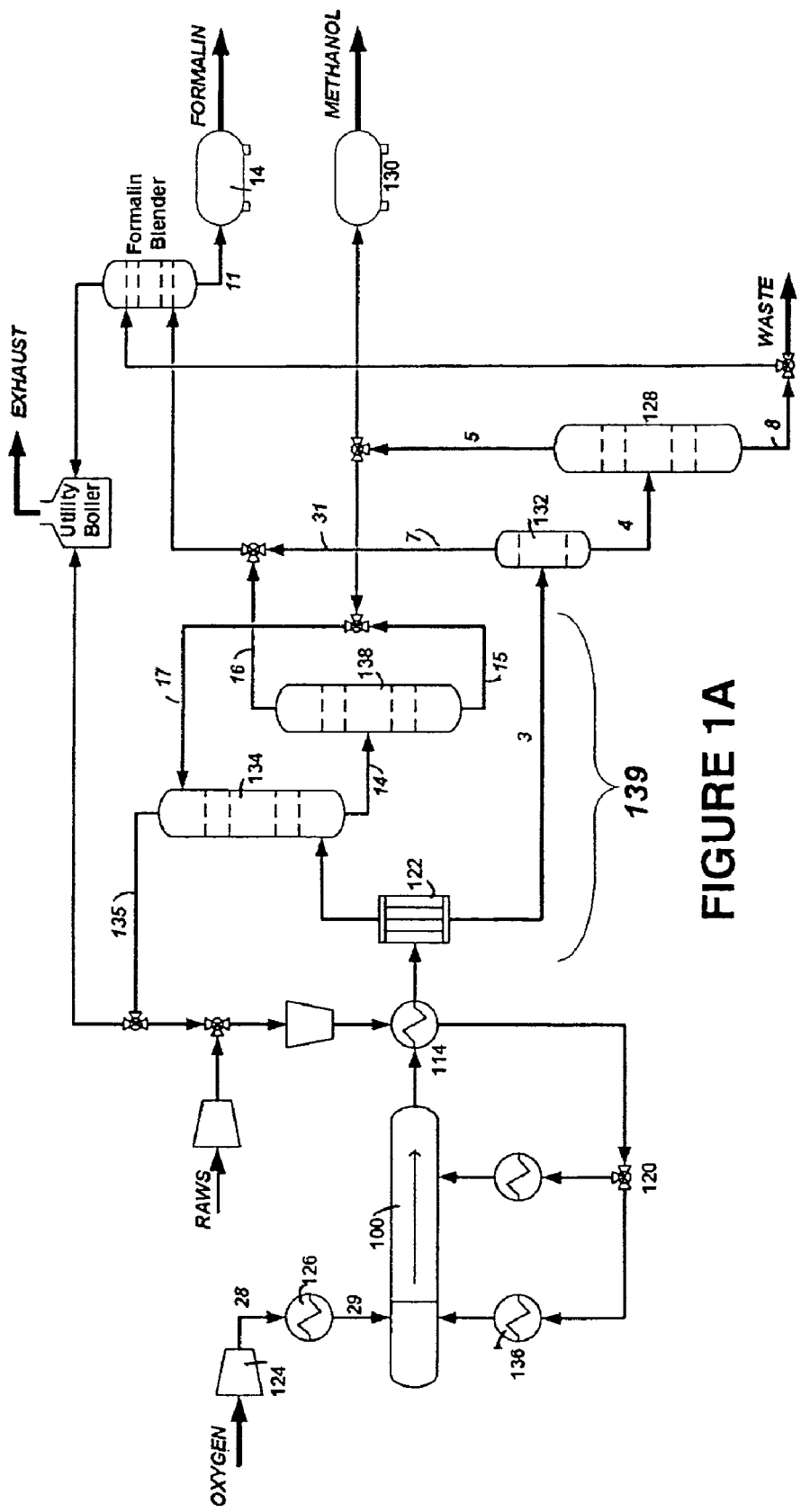
FIGS. 1A and 1B are views schematically showing a system of an apparatus for producing methanol in accordance with the present teachings.
Figure 1B:
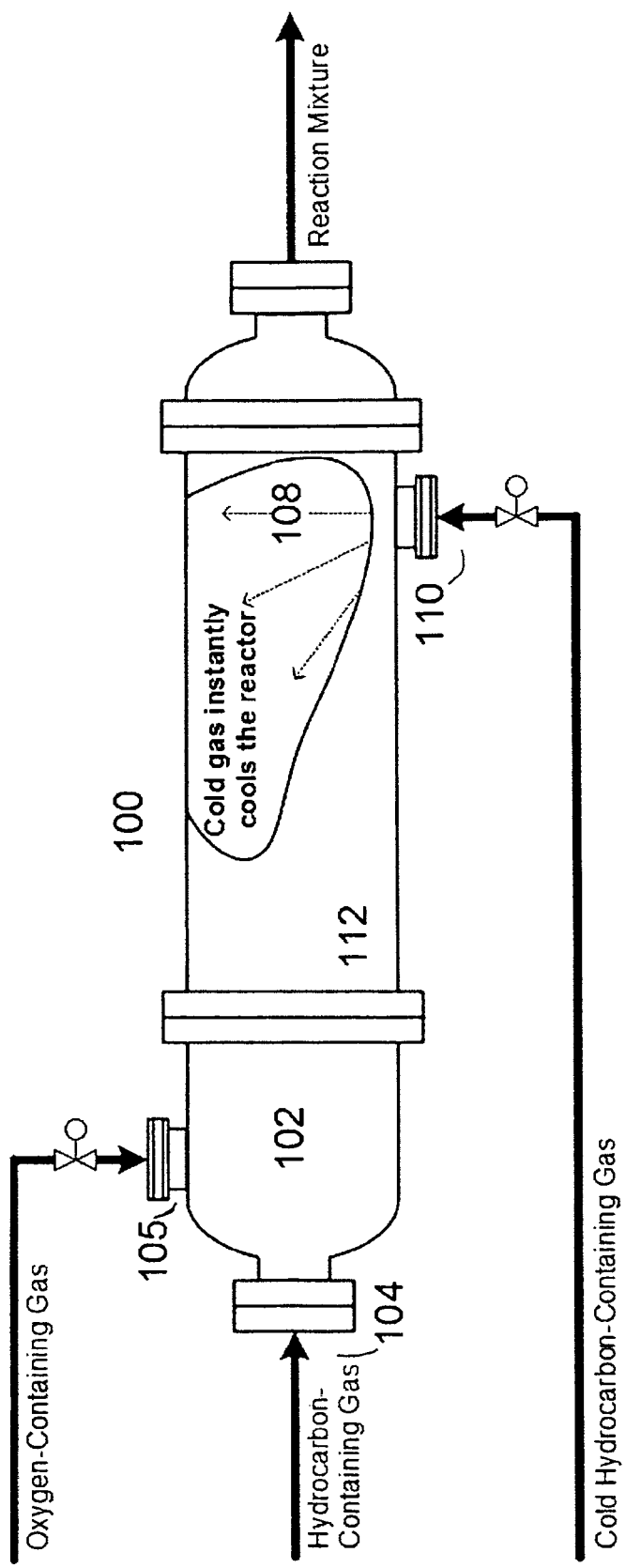

An apparatus for producing methanol in accordance with the present invention has a reactor 100 which facilitates a gas phase oxidation of a hydrocarbon-containing gas is shown in FIGS. 1A and 1B. FIG. 1B details the inputs and outputs of the reactor. The reactor 100 has a reaction zone 102 which is provided with a device 104 for introducing a heated hydrocarbon-containing gas stream and a device 105 for introducing an oxygen-containing gas. As explained in detail below, the oxygen-containing gas preferably has greater than 80% oxygen content to reduce the accumulation of inert gases by the recycling process.

The reactor 100 further has a regulation zone 108 provided with an optional device 110 for introducing a cold hydrocarbon-containing gas stream for reducing the temperature of reaction during operation of the apparatus. In addition, the reactor 100 is provided with thermal pockets 112 for control and regulation of temperatures in corresponding zones, provided for example with thermocouples.

The apparatus has a device 114 for cooling the reaction mixture before separation. Additionally, the partial condenser 122 incorporates a gas-liquid heat exchanger to further reduce the temperature of the products. The condenser 122 separates $H_2O$ and alcohols from a hydrocarbon-$CO_2$ mixture. The partial condenser 122 is preferably isobaric, as opposed to isothermal, to avoid pressure losses. The product stream enters, and liquid stream and gaseous stream exit the condenser 122.

Block 139 represents equipment which is configured to separate contaminants and products from a hydrocarbon-containing recycle gas component. In this regard, the equipment 139 is configured to remove $CO_2$ from the reduced product stream. The equipment 139 can take the form of a purge valve, absorber, membrane separator, or an adsorber. It is envisioned the equipment 139 can be used to regulate the percentage of other non-reactive components such as $N_2$ with, for example, a purge valve.

In the event the system is configured to recover formaldehyde, the gaseous reduced product stream leaves the isobaric condenser 122 and is passed to the scrubber 134. Other potential methods which can be utilized use materials such as various amines known to remove $CO_2$ and formaldehyde.

To fulfill the minimum absorption requirements, modification of the flow rate of methanol or operating temperature of the scrubber column can be used. If it is desirable to operate at extremely low absorbent flow rates, then a lower temperature can be utilized, for example 0° C. If it is desirable to operate at ambient temperatures or temperatures achievable via cooling water, then a high flow rate can be utilized, for example, ten times that of the flow rate for 0° C. In either scenario, the pregnant methanol absorbent stream 14 is completely regenerated by the formaldehyde distillation column 138. Optionally, the stream 14 from the scrubber 134 can be passed through the condenser 122 to provide cooling of the product stream and preheating of the methanol recycle to improve the energy efficiency of the formaldehyde distillation column 138.

The reactor 100 is connected with a compressor 124 and heater 126 for supply of compressed and heated oxygen-containing gas. The raw hydrocarbon-containing gas is mixed with cleaned hydrocarbon gas from the scrubber 134 and is heated using a heater 136. In the event the raw hydrocarbons have a high $CO_2$ content, the raw hydrocarbons can be mixed with the reduced product hydrocarbon stream from the condenser 122 prior to the entry of the scrubber 134 for removal of contaminant gases prior to entering the reactor.

The apparatus further has a unit for rectification of methanol which includes a flash drum 132, rectification column 128, and a vessel 130 from which methanol is supplied to storage or further processing. This rectification column 128 is used to separate methanol (light-key component) from ethanol (heavy-key component) and water (non-key component).

As before, it is desirable for a portion of the heavy key to enter the distillate stream (as dictated by commercial specification for formalin). For methanol rectification, 99% or higher purity is typical and 99.999% is achievable with multiple columns. Stream 4 enters the column and the distillate, stream 5, and bottoms, stream 8, exit the column in liquid phase. Stream 8 has some amount of ethanol (and perhaps methanol, if ultra pure methanol was produced) and will be used as the basis of the aqueous makeup of the commercial formalin stream (stream 11). In this manner, some of the ethanol is recovered before the remainder is discarded in the liquid waste stream.

Disposed between the column 128 and the condenser 122 is a flash drum 132 for removal of $CO_2$ and formaldehyde from the liquid product stream. The purpose of the flash drum 132 is to drop the pressure to an appropriate level before entry into the methanol rectification column 128 and to substantially remove any dissolved gases, typically $CO_2$ and formaldehyde, from the liquid product stream.

In operation, the raw hydrocarbon-containing gas stream with a methane content for example up to 98% and the reduced hydrocarbon product stream are supplied from an installation for preparation of gas or any other source to the heater 136, in which it is heated to temperature 430-470° C. The heated hydrocarbon-containing gas is then supplied into the reaction zone 102 of the reactor 100. Compressed air with pressure, for example, of 7-8 MPa and with a ratio 80% to 100% and, preferably, 90% to 95% oxygen is supplied by the compressor 124 also into the reaction zone 102 of the reactor 100. Oxidation reaction takes place in the reaction zone 102 of the reactor 100. Between 2% and 3% $O_2$ of the total volume of the reactants are reacted with the heated hydrocarbon-containing gas stream as previously described. To limit the amount of $N_2$ within the system, for example to less than 30%-40%, or reduce the requisite size of the purge stream to achieve the same, the $O_2$ stream is preferably substantially pure, thus limiting the amount of $N_2$ entering the system.

An optional second stream of cold or in other words a lower temperature coolant than the gases in the reactor is supplied through the introducing device 108 into the regulation zone of the reactor 100. This stream is regulated by the regulating device 120, which can be formed as a known gas supply regulating device, regulating valve or the like. This cold stream can be, for example, composed of a raw hydrocarbon stream, a recycled stream, or a portion or combination of the two. The regulator is configured to adjust the volume or pressure of cold hydrocarbon-containing gas based on system parameters such as, but not limited to, pressure, temperature or reaction product percentages down stream in the system.

The coolant, which is supplied from a coolant source, functions to reduce the temperature of the partially oxidized methane to reduce the continued oxidation or decomposition of formaldehyde. This coolant can be any material which can easily be separated from the reaction product stream. For example, as better described below, the coolant can be an unheated hydrocarbon or methane containing gas stream.

Preferably, the coolant can be any non-oxidizing material which can be easily separated from the reaction products. In this regard, the coolant can be gaseous or an aerosoled or misted liquid of, for example, $CO_2$, formaldehyde, methanol, water or steam. It is additionally envisioned that the coolant can further be a mixture of recycled reaction products, water, steam, and/or raw hydrocarbon gases.

Depending on the intended mode of operation of the apparatus, in particular the intended production of methanol or methanol and formaldehyde, the reaction mixture is subjected to the reaction in the reactor without the introduction of the cold hydrocarbon-containing gas if it is desired to produce exclusively methanol. The introduction of the cold hydrocarbon-containing gas is used when it is desired to produce methanol and formaldehyde. By introduction of the cold hydrocarbon-containing gas, the temperature of the reaction is reduced for example by 30-90° so as to preserve the content of formaldehyde into the separated mixture by reducing the decomposition of the formaldehyde to $CO_2$.

The reaction mixture is supplied into the heat exchanger 114 for transfer of heat to the reactor input stream from the reaction mixture exiting the reactor, and after further cooling is supplied within partial condenser 122. Separation of the mixture into high and low volatility components, (dry gas and raw liquid, respectively) is performed in the partial condenser 122 which may absorb at least some of the formaldehyde into the raw liquid stream as desired. The dry gas is forwarded to a scrubber 134, while the raw liquids from the condenser 122 are supplied to the flash drum 132.

The scrubber 134 functions to remove the $CO_2$ and formaldehyde from the dry gas stream. In this regard, the scrubber 134 uses both $H_2O$ and methanol at between 7-8 MPa pressure and between about 0° C. and about 50° C. to absorb $CO_2$ and formaldehyde. Once the $CO_2$ and formaldehyde are removed, the reduced stream of hydrocarbon gas is recycled by mixing the reduced stream with the raw hydrocarbon-containing gas stream either before or within the reactor, as desired. The raw hydrocarbon and reduced streams, individually or in combination, are then inputted into the reaction chamber 100 at input 104 or input 110 after being heated by heat exchanger 116 and heater 136 as previously described.

The rectification column is used to separate carbon dioxide (non-key component) and formaldehyde (light-key component) from methanol (heavy-key component) and water (non-key component). The pregnant methanol steam, stream 14, enters the rectification column and is separated into a formaldehyde distillate, stream 16, and a bottoms stream, stream 15. Some amount of methanol in the distillate stream is desirable since methanol is used as a stabilizer for the production of commercial grade formalin (6-15% alcohol stabilizer, 37% formaldehyde, and the balance being water). By allowing a portion of the heavy key into the distillate stream the separation is more easily achieved; furthermore, process losses typically experienced during absorbent regeneration are subsequently nullified as methanol within the distillate is used for formalin production. Stream 15 is supplemented by stream 31 so as to replace any methanol which was transferred to the distillate stream, stream 16. Combining stream 31 and stream 15 results in stream 17, which then returns to the scrubber 134 as regenerated methanol absorbent. Meanwhile, the formaldehyde distillate, stream 16, combines with the vapors from flash drum 132, stream 7, to form a mixture of formaldehyde, methanol, and carbon dioxide.

The formaldehyde, water, methanol and $CO_2$ removed by scrubber 134 are passed to formaldehyde rectification column 138. Column 138 removes formaldehyde and $CO_2$ from the methanol-water stream. Small amounts of methanol are combined with produced methanol and are inputted into the scrubber 134 to remove additional amounts of $CO_2$ and formaldehyde from the reduced hydrocarbon stream.

Free or non-aqueous formaldehyde is allowed to remain in the gas phase by operation of the isobaric condenser 122. The liquid methanol product stream, or raw liquids, would then comprise methanol, ethanol, and water by allowing formaldehyde to remain in the gaseous stream. In this case, the liquid stream exiting the isobaric condenser 122 can bypass the formaldehyde rectification portion of the process and enter the methanol rectification column after having optionally passed through the flash drum 132.

Figure 2:
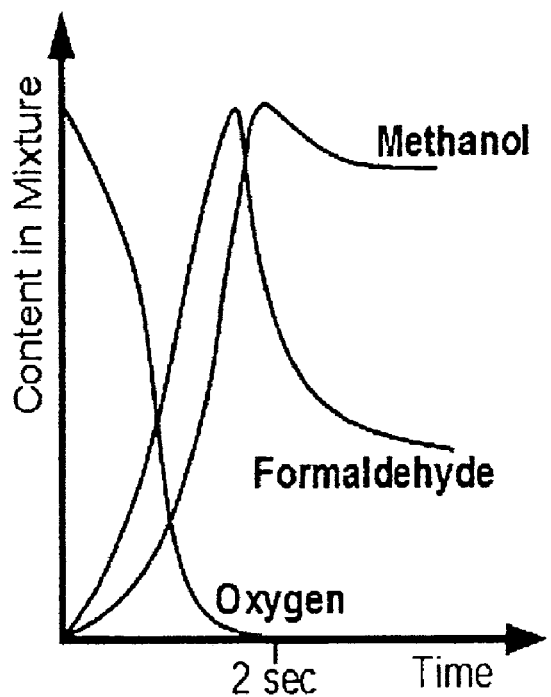
FIGS. 2 and 3 are views illustrating concentrations of oxygen, formaldehyde and methanol during reactions in accordance with the prior art and in accordance with the present invention correspondingly.
Figure 3:
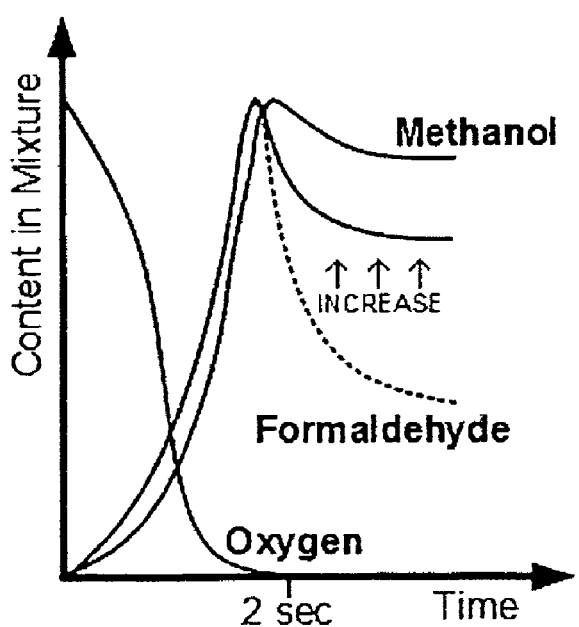

FIGS. 2 and 3 show diagrams of the concentration of oxygen, formaldehyde and methanol in reactions without cooling and with cooling, respectively.

As can be seen from FIG. 2, approximately after 2 sec, oxygen is burnt completely. At this moment the reaction temperature reaches its maximum and methanol and formaldehyde are produced in their respective proportions within the reaction mixture. Methanol is a more stable product at the end of the reaction and its concentration remains substantially stable after reaching its maximum concentration. Formaldehyde is less stable, and therefore with a temperature increase (the temperature increases until oxygen is burnt completely) its concentration somewhat reduces.

In the reaction with the cooling shown in FIG. 3, via the introduction of cold gas when the formation of methanol and formaldehyde is completed, the temperature of a final period of the reaction is reduced so as to inhibit the decomposition of formaldehyde.

Figure 4:
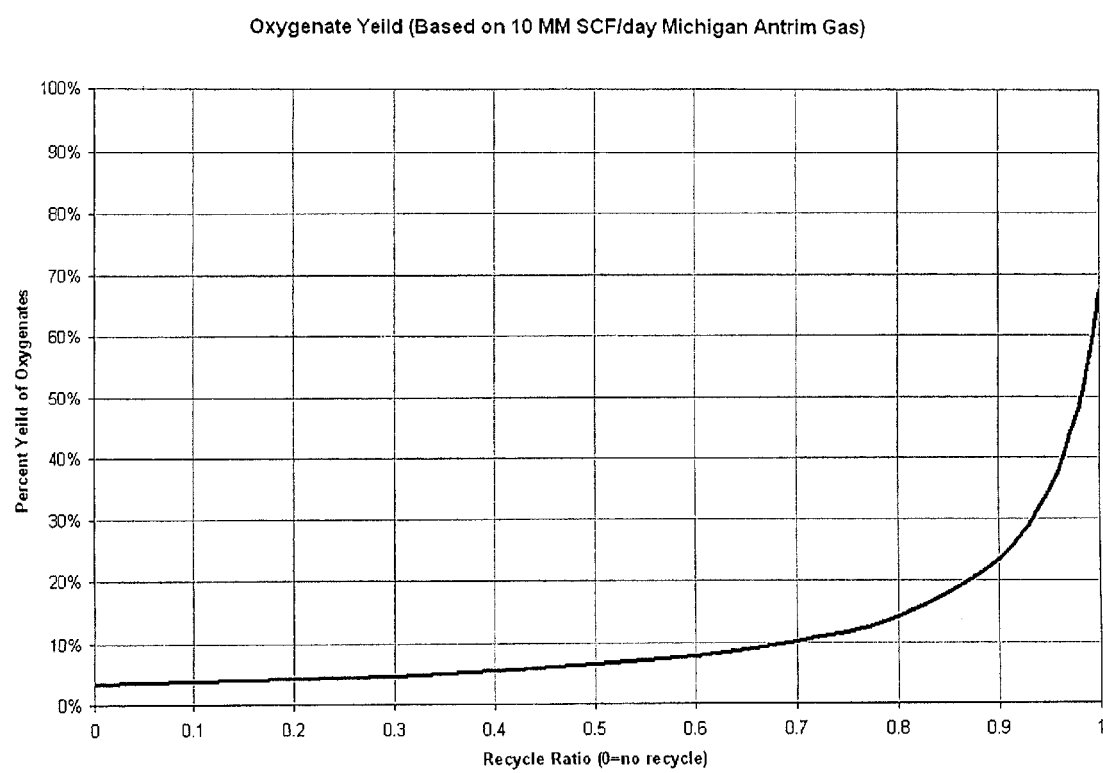
FIG. 4 represents a graph depicting the yield oxygenates of the system as a function of recycle ratio.

FIG. 4 represents a graph depicting the yield of oxygenates for the system as a function of the recycle ratio of the recycling hydrocarbon gasses. Shown is a graph depicting the use of Michigan Antrim gas having 97% $CH_4$ and 1% $N_2$. In this regard, the graph shows a significant increase in product yield using the same input stream and with little increase in capital costs. As the system efficiently manages pressure and integrates process energy usage, energy requirements are minimized, thus increasing the overall system economics.

Figure 5:
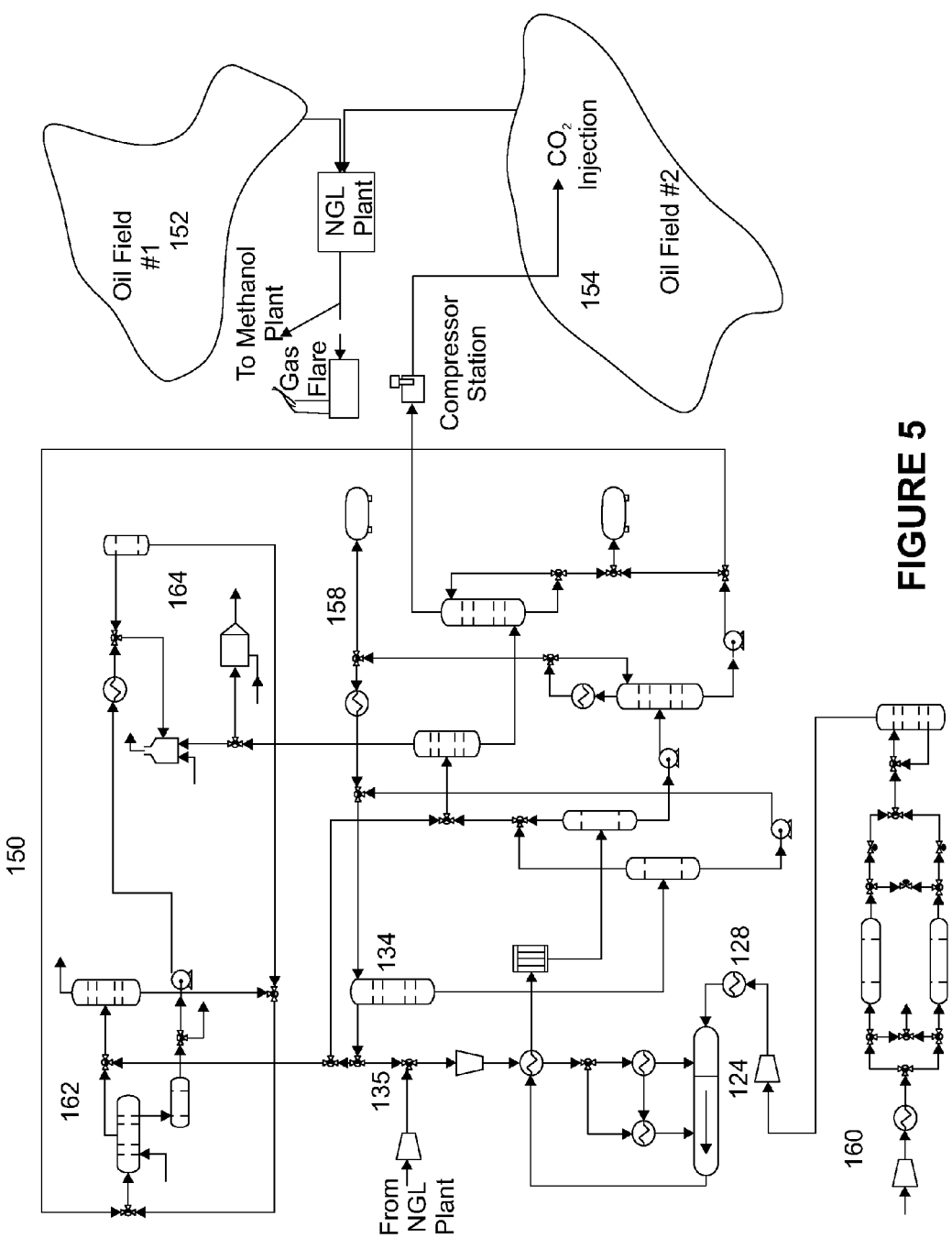
FIG. 5 represents an alternate methane to methanol plant according to the teachings of the present invention.

FIG. 5 represents an alternate methane to methanol plant 150. The plant 150 is positioned to process methane from gas being discharged from either a combined oil and gas field 152 or the gas field 154. The plant 150, which is preferably located in close proximity to the well bore, is generally formed of a gas processing plant 156, a liquid processing plant 158, and an oxygen producing plant 160. Additionally associated with the plant 150 are waste water treatment and utility plants 162 and 164.

Figure 6:
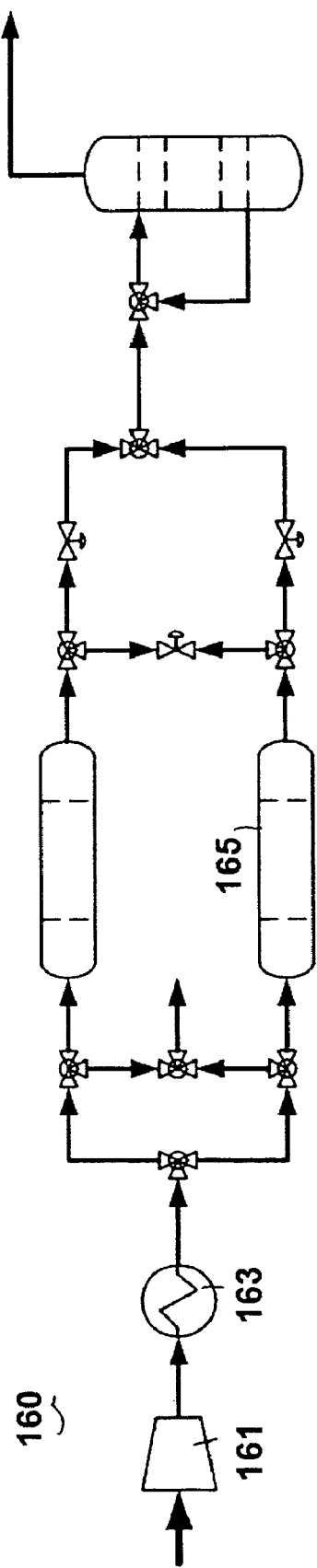
FIG. 6 represents an optional oxygen producing plant shown in FIG. 5.

As shown in FIG. 6, an optional oxygen producing plant 160 can be used to assist in the regulation of the partial oxidation of the hydrocarbon stream in the reactor 100. The oxygen producing plant 160 has a compressor 161 coupled to a heat exchanger 163 which functions to prepare the compressed oxygen for injection into a plurality of absorbers 165. After passing through the absorbers, the produced oxygen stream is compressed and forwarded directly to the reactor 100.

Figure 7:
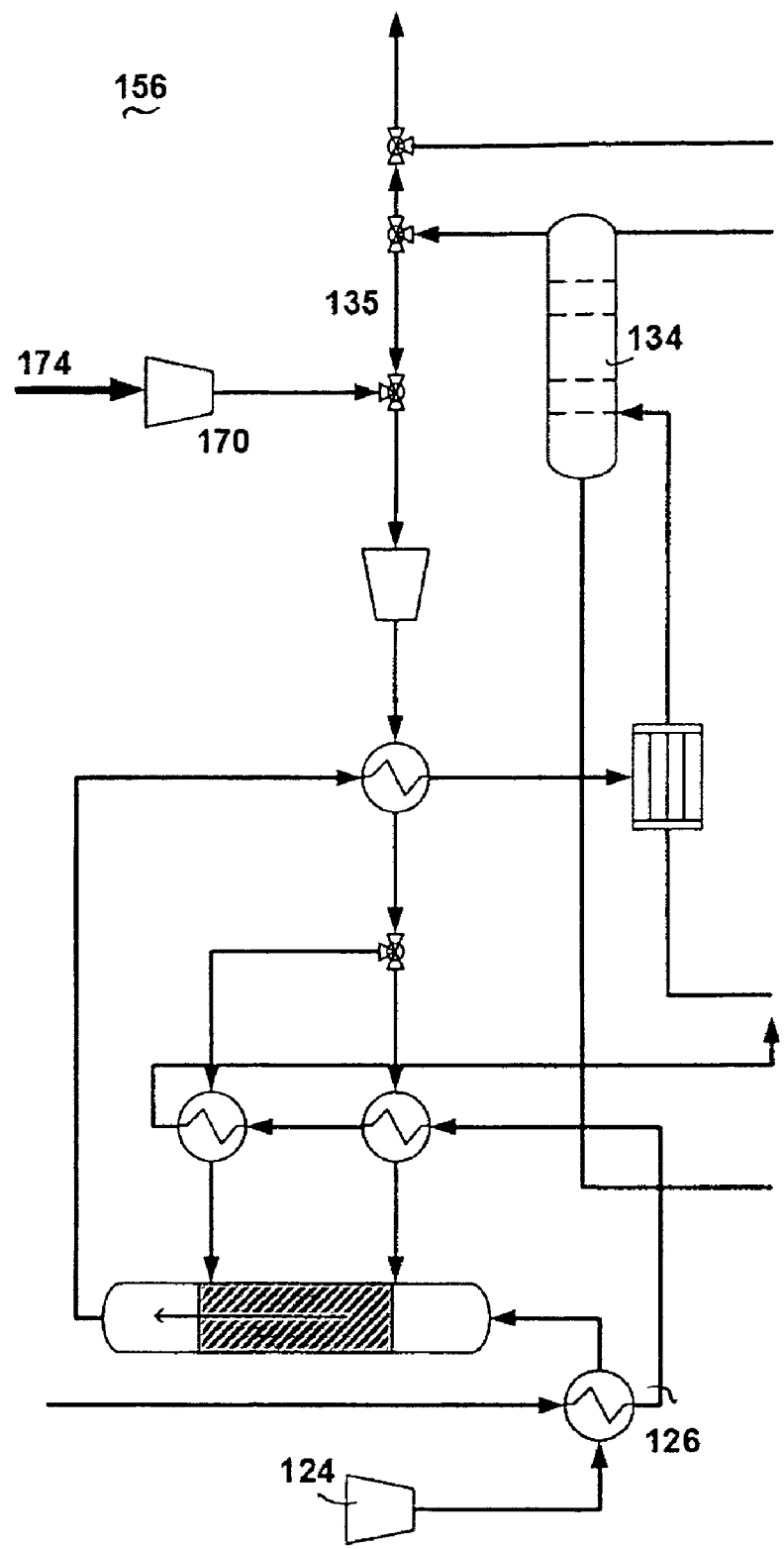
FIG. 7 depicts a gas processing portion of the plant shown in FIG. 5.

With general reference to FIG. 7, the gas processing portion of the plant 156 generally functions as described above (see FIGS. 1A and 1B). In this regard, the gas processing plant 156 has compressors 170 and 172 for raising the pressure of a cleaned incoming hydrocarbon stream 174. This stream 174 is then divided and reacted with oxygen in the reactor 100 to partially oxidize methane as described above. It is envisioned that the parameters such as time of reaction and temperature and pressure within the reactor can be adjusted to selectively control the amount of $CO_2$, $H_2O$, formaldehyde and methanol which is produced in the reactor 100. The reaction products 176 from the reactor are then transferred to the liquid processing plant 158.

Figure 8:
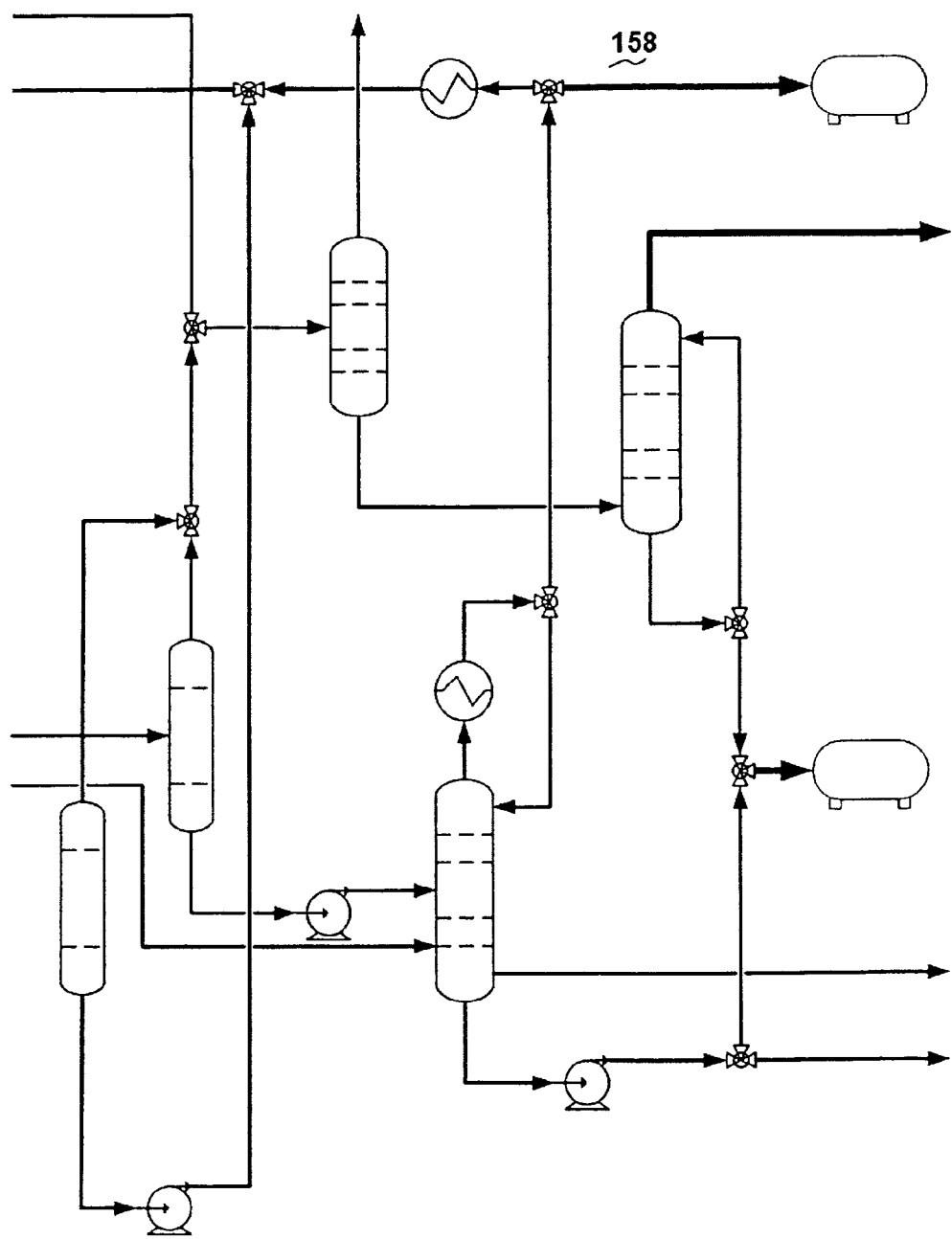
FIG. 8 represents the liquid processing portion of the plant shown in FIG. 5.

As shown in FIG. 8, the liquid processing plant 158 generally functions as described above to separate the methanol and formaldehyde from the reaction product stream 176. Shown are associated distillers, blenders and flash drums which are used to separate the constituent materials of the reaction product stream as described in detail above. Specifically, $CO_2$ is removed from the reaction product stream as are methanol and, if desired, formaldehyde. The scrubber 134 (see FIG. 5) prevents the accumulation of $CO_2$ and allows the physical capture of formaldehyde. The scrubber 134 can utilize a mixture of methanol and water to physically absorb formaldehyde and $CO_2$ from the hydrocarbon gas recycle loop 135. The efficiency of the scrubber 134, which can operate adequately without refrigeration, is made possible due to the high operating pressure of the recycle loop 135. This is opposed to cryogenically low temperatures utilized by traditional absorption processes. The gases enter the scrubber 134 as a "dirty" gas with some amount of formaldehyde and $CO_2$ present. These components will only be present in relatively dilute amounts, so the duty of the methanol absorbent is also relatively small.

As previously mentioned, it is envisioned that the output of the reactor can be selectively adjusted so as to minimize the amount of formaldehyde being produced by the gas process portion of the plant 156. While the $CO_2$ can be vented, it is specifically envisioned that the $CO_2$ from the reaction products can be injected, at a predetermined distance from the well, into the ground to increase the output of the well. In this regard, it is envisioned that the $CO_2$ can be injected at any appropriate distance from the well so as to allow for the increase of subterranean pressures to increase the gas or oil output of the well. Additionally, it is envisioned that the $CO_2$ can be injected into the casement of the wellbore or in the near-wellbore zone, to increase the output of the gas or oil and gas producing well.

While shown as a land based plant, it is specifically envisioned that the plant 100 can be associated with an off-shore oil rig. In this regard, the plant 100 would either be on the off-shore rig or would be a predetermined short distance from the rig, such as immediately adjacent to the off-shore rig on a floatable platform. In the case of an off-shore rig, which is producing natural gas, it is envisioned that the methanol converted from the methane containing hydrocarbon stream would be injected into a second portion of the methane containing hydrocarbon stream to improve the flow of the hydrocarbon stream from the off-shore oil well to land. This methanol is injected to reduce the formation of hydrates within the piping. The methanol associated with the natural gas would then be removed from the hydrocarbon containing stream after the stream reaches the shore.

It is further envisioned that any of the other reaction products, namely, $CO_2$, water or methanol can be injected directly into the hydrocarbon containing subterranean formations surrounding the platform or a land-based well. Specifically, it is envisioned that methanol can be injected into hydrate structures surrounding the well so as to increase the output of natural gas from a natural gas producing well.

Returning briefly to FIG. 5, it is envisioned that the $CO_2$ can be injected into one portion of the well while methanol or other reaction products can be injected into other portions of the well. In situations where the natural gas may be stranded or may have nitrogen contents of greater than 4%, facilities may be provided to manage nitrogen build-up in the recycle loop. When outputs of any particular well 152, 154 are low, it is envisioned that a single plant 100 having a truncated process can be used. In these situations, only portions of the facility related to the partial oxidation of the hydrocarbon stream and associated facilities to remove $CO_2$ will be used near the well.

Removed $CO_2$ can be collected, vented or reinjected into the ground. Immediately after removal of the natural gas and associated $CO_2$ by the scrubber, the remaining liquid products can be transported in liquid form from the well site to another location for separation of formaldehyde, methanol and water from the waste stream. In this regard, it is envisioned a centralized liquid processing plant to finalize the processing of the liquid processes (158) can be located at a significant distance from the stranded natural gas locations. This allows for the use of a centralized liquid process facility 158. It is also envisioned that the conditions of the reactor can be adjusted to produce a liquid phase which contains a commercial grade of formalin.

It will be understood that each of the elements described above, or two or more together, may also find a useful application in other types of methods and constructions differing from the types described above. While the invention has been illustrated and described as embodied in the method of and apparatus for producing methanol, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention. What is claimed as new and desired to be protected by Letters Patent is set forth in the appended claims.

What is claimed is:

1. A method of producing methanol comprising:
converting a first methane containing gas from a well into reaction products using a partial oxidation reaction, the reaction products including methanol, $CO_2$, $H_2O$, ethanol, and formaldehyde;
separating the $CO_2$ from the reaction products; and
injecting the $CO_2$ at a predetermined distance from the well into the ground to increase output of the well.

2. The method according to claim 1 wherein converting the first methane containing gas is accomplished while adjusting amounts of $CO_2$, $H_2O$, and formaldehyde produced by adjusting feed composition and process parameters so as to influence selectivity of the reaction.

3. The method according to claim 1 wherein converting methane gas to methanol includes providing an oxygen containing gas; providing the first methane containing gas; reacting the oxygen containing gas with the methane containing gas to form a reaction product stream; and directly mixing a coolant with the reaction product stream to adjust the degree of oxidation of formaldehyde, thereby increasing the proportion of $CO_2$ and $H_2O$ to formaldehyde.

4. The method according to claim 3 wherein directly mixing the coolant includes directly mixing a second methane containing gas stream into the reaction product stream.

5. The method according to claim 4 wherein at least a portion of the first and second methane containing gas streams are taken from the well.

6. The method according to claim 5 wherein the first and second methane containing gas streams are taken from the well.

7. A method of producing methanol comprising:
partially oxidizing a hydrocarbon gas containing stream to form a reaction product stream comprising $CO_2$;
separating $CO_2$ from the reaction product stream; and
injecting the $CO_2$ into the ground within a predetermined distance from a well.

8. The method according to claim 7 wherein the hydrocarbon gas containing stream comprises methane.

9. The method according to claim 7 wherein partially oxidizing the hydrocarbon gas includes reacting the methane containing stream with an oxygen containing stream to form the reaction product stream.

10. The method according to claim 9 further comprising injecting a second hydrocarbon gas from the reaction product stream to regulate the reaction product.

11. The method according to claim 10 wherein the reaction product stream comprises methanol, formaldehyde, $H_2O$ and $CO_2$.

12. The method according to claim 11 further comprising reacting the reaction stream to convert the formaldehyde to $CO_2$, and $H_2O$.

13. A method of producing methanol comprising:
partially oxidizing a hydrocarbon gas containing stream from a well to form a reaction product stream comprising methanol and $CO_2$;
separating $CO_2$ from the reaction product stream; and
injecting the $CO_2$ into the ground within a predetermined distance from the well.

14. The method according to claim 13 wherein the hydrocarbon gas containing stream comprises methane having greater than 4% nitrogen.

15. The method according to claim 14 wherein partially oxidizing the hydrocarbon gas includes reacting the methane containing stream with an oxygen containing stream to form the reaction product stream within a plurality of reactors to minimize the formation of formaldehyde to below 0.5%.

16. The method according to claim 15 further comprising injecting a second gas from the reaction product stream to regulate the reaction product.

17. The method according to claim 16 wherein the reaction product stream comprises methanol, formaldehyde, $H_2O$, ethanol and $CO_2$.

18. The method according to claim 17 further comprising reacting the reaction stream to convert the formaldehyde to $CO_2$, and $H_2O$.

19. A method of producing methanol comprising:
partially oxidizing a first portion of a hydrocarbon gas containing stream from an off-shore hydrocarbon producing well, at a first off-shore location, to form a reaction product stream comprising $CO_2$ and methanol;
separating $CO_2$ from the reaction product stream; injecting the $CO_2$ into the ground within a predetermined distance from the off-shore hydrocarbon producing well; and
injecting the methanol into a second portion of the hydrocarbon gas containing stream at a second off-shore location.

20. The method according to claim 19 wherein partially oxidizing the first portion of the hydrocarbon gas containing stream is reacting the methane containing gas stream with an oxygen containing stream to form the reaction product stream.

21. The method according to claim 20 further comprising directly injecting a coolant into the reaction product stream to regulate reaction products of the reaction product stream.

22. The method according to claim 19 further comprising regulating the amount of nitrogen in the first portion of the hydrocarbon gas containing stream.

23. The method according to claim 19 further comprising injecting reaction products into the near well bore region.

24. The method according to claim 22 wherein the reaction products comprise methanol.

25. A method of producing methanol comprising:
providing a hydrocarbon gas containing stream from a well;

regulating the amount of nitrogen within the hydrocarbon containing stream;

partially oxidizing a first portion of the hydrocarbon gas containing stream to form a reaction product comprising methanol and $CO_2$;

separating the $CO_2$ from the reaction product; and injecting the $CO_2$ into the ground within a predetermined distance of the well.

26. The method according to claim 25 further including removing hydrocarbon components greater than or equal to in molecular weight than propane from the hydrocarbon containing stream prior to partial oxidation of the first portion.

27. The method according to claim 26 further comprising separating methanol from the reaction product.

28. The method according to claim 27 further comprising injecting the methanol into at least one of the near well bore or a second portion of the hydrocarbon containing gas.

29. The method according to claim 26 wherein regulating the amount of nitrogen within the hydrocarbon containing stream is diluting the hydrocarbon containing stream.

* * * * *